(12) United States Patent
Hsu

(10) Patent No.: US 11,730,620 B2
(45) Date of Patent: Aug. 22, 2023

(54) FLAT FOOT ORTHOSIS

(71) Applicant: Wen-Hua Hsu, Kaohsiung (TW)

(72) Inventor: Wen-Hua Hsu, Kaohsiung (TW)

( * ) Notice: Subject to any disclaimer, the term of this patent is extended or adjusted under 35 U.S.C. 154(b) by 0 days.

(21) Appl. No.: 17/846,445

(22) Filed: Jun. 22, 2022

(65) Prior Publication Data

US 2022/0313468 A1 Oct. 6, 2022

Related U.S. Application Data

(62) Division of application No. 16/286,078, filed on Feb. 26, 2019, now abandoned.

(30) Foreign Application Priority Data

Mar. 2, 2018 (TW) .................. 107107059

(51) Int. Cl.
*A61F 5/01* (2006.01)
*A43B 7/28* (2006.01)
(Continued)

(52) U.S. Cl.
CPC .............. *A61F 5/0127* (2013.01); *A43B 7/28* (2013.01); *A61F 5/0111* (2013.01);
(Continued)

(58) Field of Classification Search
CPC ......... A43B 5/1691; A43B 13/00; A43B 7/28; A43B 7/14; A43B 7/20; A61F 13/066;
(Continued)

(56) References Cited

U.S. PATENT DOCUMENTS

| 4,313,433 A | 2/1982 | Cramer |
| 4,644,940 A | 2/1987 | Nakamura |

(Continued)

FOREIGN PATENT DOCUMENTS

| CN | 101627838 A | 1/2010 |
| CN | 102421309 A | 4/2012 |

(Continued)

OTHER PUBLICATIONS

WO-2010131864-A2 machine translation (Year: 2010).*
JPH1176283A machine translation (Year: 1999).*
KR101500297B1 machine translation (Year: 2015).*

*Primary Examiner* — Caitlin A Carreiro
(74) *Attorney, Agent, or Firm* — Birch, Stewart, Kolasch & Birch, LLP

(57) ABSTRACT

A flat foot orthosis has two bodies and a pelvis portion. Each one of the two bodies has a wearing space, a foot portion, an ankle portion, a shank portion, a knee portion, a thigh portion, a toe portion, a hallux valgus region, a substrate, a first elastomer, and a second elastomer. The substrate and the first elastomer are disposed adjacent to each other, and surround the wearing space. The substrate extends from the toe portion to the thigh portion. The first elastomer spirally extends from an instep of the foot portion to the thigh portion through the rest. The two first elastomers surround and fetter where the wearer's pelvis and the wearer's waist meet. The second elastomer extends from the hallux sheath, is connected to the first elastomer, and wraps over the hallux valgus region.

1 Claim, 18 Drawing Sheets

(51) Int. Cl.
*A61F 5/058* (2006.01)
*A61F 5/14* (2022.01)

(52) U.S. Cl.
CPC .............. *A61F 5/0585* (2013.01); *A61F 5/14* (2013.01); *A61F 2005/0132* (2013.01)

(58) Field of Classification Search
CPC .. A61F 2005/0132; A61F 5/00; A61F 5/0111; A61F 5/0127; A61F 5/0102; A61F 5/01; A61F 5/0585; A61F 5/14; A61F 5/0195; A41D 1/06
USPC .......... 36/43–44, 88, 89, 104; 128/845, 846, 128/882; 602/5, 23, 27, 60–61, 65
See application file for complete search history.

(56) References Cited

U.S. PATENT DOCUMENTS

| | | |
|---|---|---|
| 4,844,058 A | 7/1989 | Vogelbach |
| 2007/0049857 A1* | 3/2007 | Quinn ................... A61F 5/0111 602/27 |
| 2012/0238929 A1 | 9/2012 | Grunden et al. |
| 2015/0374529 A1 | 12/2015 | Summit et al. |
| 2016/0206462 A1 | 7/2016 | Iida |
| 2017/0079847 A1 | 3/2017 | Tsuchiya et al. |
| 2018/0021199 A1 | 1/2018 | Halbrecht |
| 2018/0333285 A1 | 11/2018 | Thor et al. |
| 2019/0192329 A1 | 6/2019 | Salloum |

FOREIGN PATENT DOCUMENTS

| | | | |
|---|---|---|---|
| CN | 103096845 A | 5/2013 | |
| CN | 203226933 U | 10/2013 | |
| CN | 107714252 A | 2/2018 | |
| EP | 0 159 679 A2 | 4/1985 | |
| JP | 5-95516 U | 12/1993 | |
| JP | H1176283 A * | 3/1999 | |
| JP | 2005-160982 A | 6/2005 | |
| JP | 2009-299236 A | 12/2009 | |
| JP | 2010-70871 A | 4/2010 | |
| JP | 2017-115256 A | 6/2017 | |
| KR | 101500297 B1 * | 3/2015 | |
| WO | WO 87/02885 A1 | 5/1987 | |
| WO | WO 01/49143 A1 | 7/2001 | |
| WO | WO-2010131864 A2 * | 11/2010 | ............... A41D 1/06 |

* cited by examiner

FLAT FOOT ORTHOSIS

CROSS REFERENCE TO RELATED APPLICATIONS

This application is a divisional application of U.S. patent application Ser. No. 16/286,078, filed on Feb. 26, 2019, which claims priority under 35 U.S.C. § 119(a) to Application No. 107107059, filed in Taiwan on Mar. 2, 2018, the disclosures of which are incorporated herein by reference.

BACKGROUND OF THE INVENTION

1. Field of the Invention

The present invention relates to an orthosis for lower limbs, and more particularly to a flat foot orthosis that may correct pronation of the foot (functional flat foot), hallux valgus, internal rotation of lower limbs, knee valgus, and pelvic tilt and torsion.

2. Description of Related Art

For most of human history, humans step on soft surfaces such as dirt, sand, or grass, the soft surfaces would conform to each foot due to pressure, and provide support for the feet. For instance, in the inspection of a footprint in sand, the lateral side of the footprint makes an indention. The medial side of the footprint does not indent, but rather the sand supports the medial arch of the foot. As a result, the support prevented pronation of feet, and prevents collapsed medial arches. This kept their bone structures aligned, and maintained a correct alignment of bones and joints and proper biomechanics.

However, in the modern society, hard surfaces such as concrete pavement do not conform to feet. So when people step on hard surfaces, the feet are exposed to increased pressure and unalign pronate. In more severe situations, bone and joint alignments of the foot may become unaligned. Ankle joints may also be affected. Talus adduction combine inversion may occur. A subtalar joint may suffer subluxation. Internal rotations of lower limbs (a tibia and a femur), knee valgus, and functional leg length inequality may occur. The internal rotation of the femur makes a femoral head of the femur backwardly push a pelvic acetabulum, and pelvic tilt will thereby occur. A tilted pelvis may lead to curved spine compensation, and subsequently functional scoliosis, unbalanced tensions of paraspine muscles and soft tissue may thereby occur. Such disordered bone and joint alignments and improper biomechanics cause symptoms such as plantar fasciitis, Achilles tendon pain, shin splint, MCL (medial collateral ligament) stretch and lateral meniscus compression, ACL (anterior cruciate ligament) stretch, patella valgus, ITB (iliotibial band) syndrome, gluteus medius dysfunction, pelvic tilt & torsion, functional leg length inequality, functional scoliosis, hip joint bursitis, prirformis syndrome, psoas major & multifidus stretch & weakness, SI (sacroiliac) joint subluxation & sacrolitis, HIVD (herniation of inter-vertebral disc), lumbar facet joint syndrome, soft tissue tightness or spondylolisthesis, shoulder elevation compensation dysfunction, CT (cervical thoracic) junction, cervical disc herniation, cervical facet joint syndrome, neck and upper back myofascial problem, TMJ (temporomandibular joint) subluxation, unilateral headache, etc.

With reference to FIGS. 17, 18A, and 18B, a foot 90 of a person is overpronated. The overpronated foot 90 causes an above-located tibia 91 to internally rotate, and a corresponding femur 92 would internally rotate as well. As a result, the corresponding knee joint 99 of the person would cause knee valgus. A femoral head 93 of the femur 92 would push an acetabulum 94 of a pelvis 95 backwardly, and further cause pelvic tilt and torsion. A spine 96 of the person becomes curved spine compensation, namely scoliosis, as a result of the tilted pelvis 95. Moreover, a scapula 97 and a clavicle 98 would be also tilted due to the scoliosis. In summary, the serial disorder of bone and joint alignments creates poor postures, and accordingly the person may suffer those aforementioned symptoms.

SUMMARY OF THE INVENTION

The main objective of the present invention is to provide a flat foot orthosis that may keep correct bone and joint alignments and proper biomechanics, and correct poor postures, and subsequent discomfort and muscular sore & pains.

The flat foot orthosis is configured for correcting a flat foot, and comprises two bodies and a pelvis portion. Each one of the two bodies has a wearing space disposed inside the respective body, a foot portion, an ankle portion, a shank portion, a knee portion, a thigh portion, a toe portion, a hallux valgus region, a substrate, a first elastomer, and a second elastomer. The foot portion has a sole located on a bottom of the foot portion, an instep located on a top of the foot portion, an arch, and a lateral side. The arch and the lateral side are located on two horizontal sides of the foot portion, wherein the arch is located on one of the two horizontal sides that faces the other one of the two bodies. Each one of the arch and the lateral side is connected to the sole and the instep. The ankle portion is connected to the foot portion. The shank portion is connected to the ankle portion. The knee portion is connected to the shank portion. The thigh portion is connected to the knee portion. The toe portion is connected to a front end of the foot portion, and has a hallux sheath. The hallux valgus region is located between the hallux sheath and the arch of the foot portion.

The substrate and the first elastomer are disposed adjacent to each other, and surround the wearing space. The substrate extends from the toe portion to the thigh portion through the foot portion, the ankle portion, the shank portion, and the knee portion. The first elastomer is a single strip, has an end located on the instep of the foot portion and configured for placement at a cuboid bone of a wearer, extends spirally from the end through the lateral side, the sole, and the arch in order, is configured for wrapping over a navicular bone of the wearer, extends through the ankle portion, is configured for placement at a talus bone of the wearer, extends through a rear side of the shank portion, obliquely extends in combination with upward and inward turns through an inner side of the knee portion, and spirally extends through the thigh portion.

The second elastomer is configured for extending from the hallux sheath at a top of the wearer's hallux, through a bottom of the wearer's hallux, further extends upwardly through and wraps the hallux valgus region, through the instep toward the ankle portion, and is connected to the first elastomer. The pelvis portion is connected to the two thigh portions of the two bodies, has an opening communicating with the wearing spaces of the two bodies, and is configured for wrapping over a hip joint of the wearer. The first elastomer of each one of the two bodies spirally extends from the thigh portion to the pelvis portion, is configured for wrapping the wearer's hip joint, intersecting with the first elastomer of the other one of the two bodies at a rear side of the wearer's hip behind the wearer's pelvis, extending and wrapping over a sacroiliac joint and an iliac crest of the wearer, and has a surrounding and fettering part located away from the end, so that the first elastomer is configured to provide a stretching and pressing force on the wearer's medial arch, pulling the wearer's medial arch. The two surrounding and fettering parts of the first elastomers of the two bodies surround and fetter where the wearer's pelvis and the wearer's waist meet.

Other objectives, advantages and novel features of the invention will be described in the following detailed description when taken in conjunction with the accompanying drawings.

DETAILED DESCRIPTION OF THE PREFERRED EMBODIMENT

Figure 1:
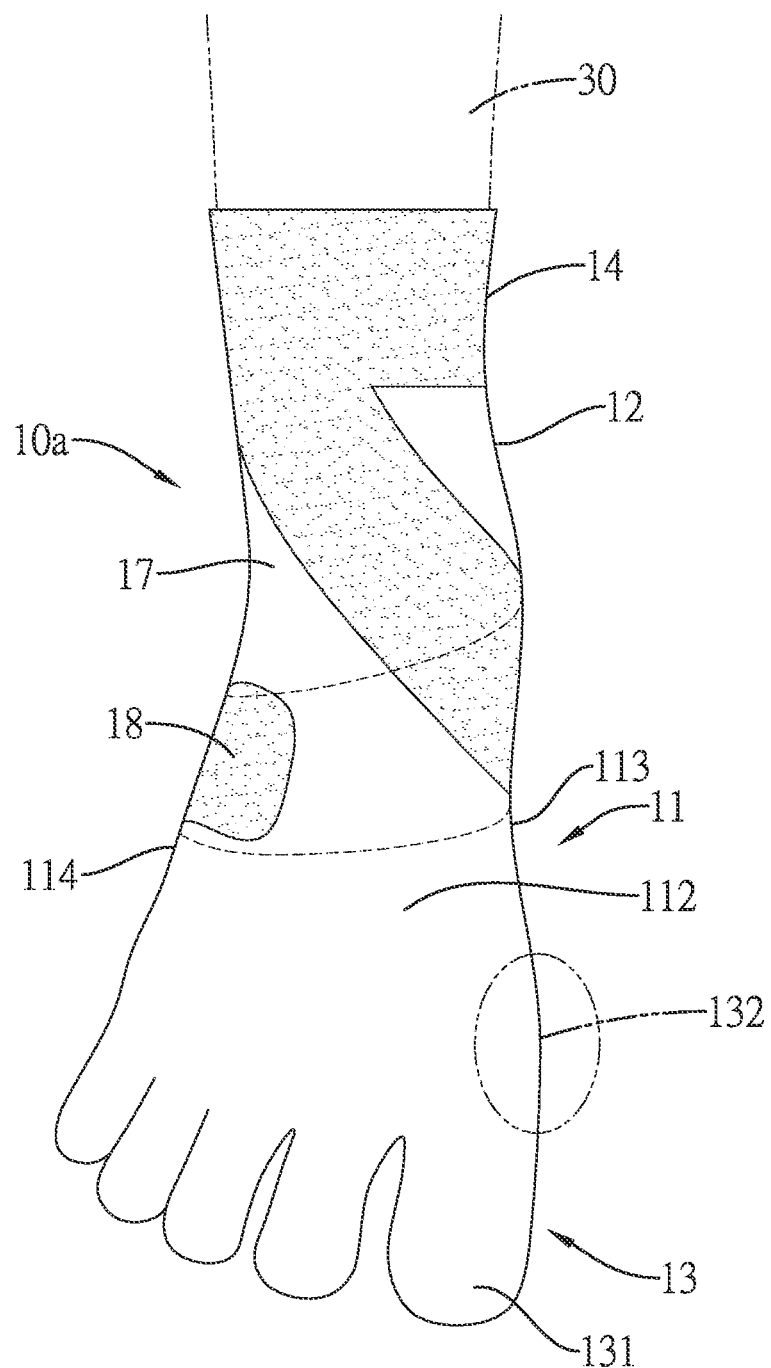
FIG. 1 is a front side view of a flat foot orthosis of a first embodiment in accordance with the present invention.
Figure 2:
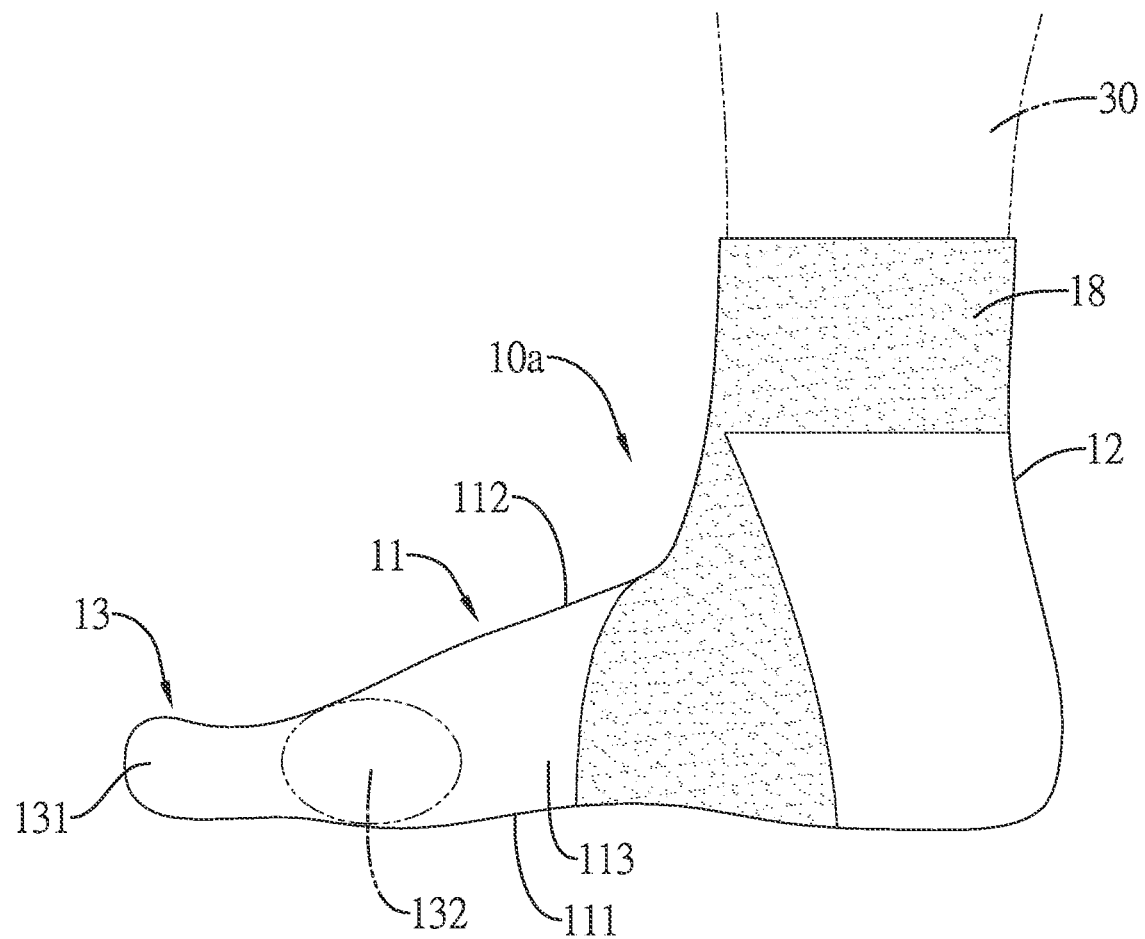
FIG. 2 is a side view of the flat foot orthosis in FIG. 1.
Figure 3:
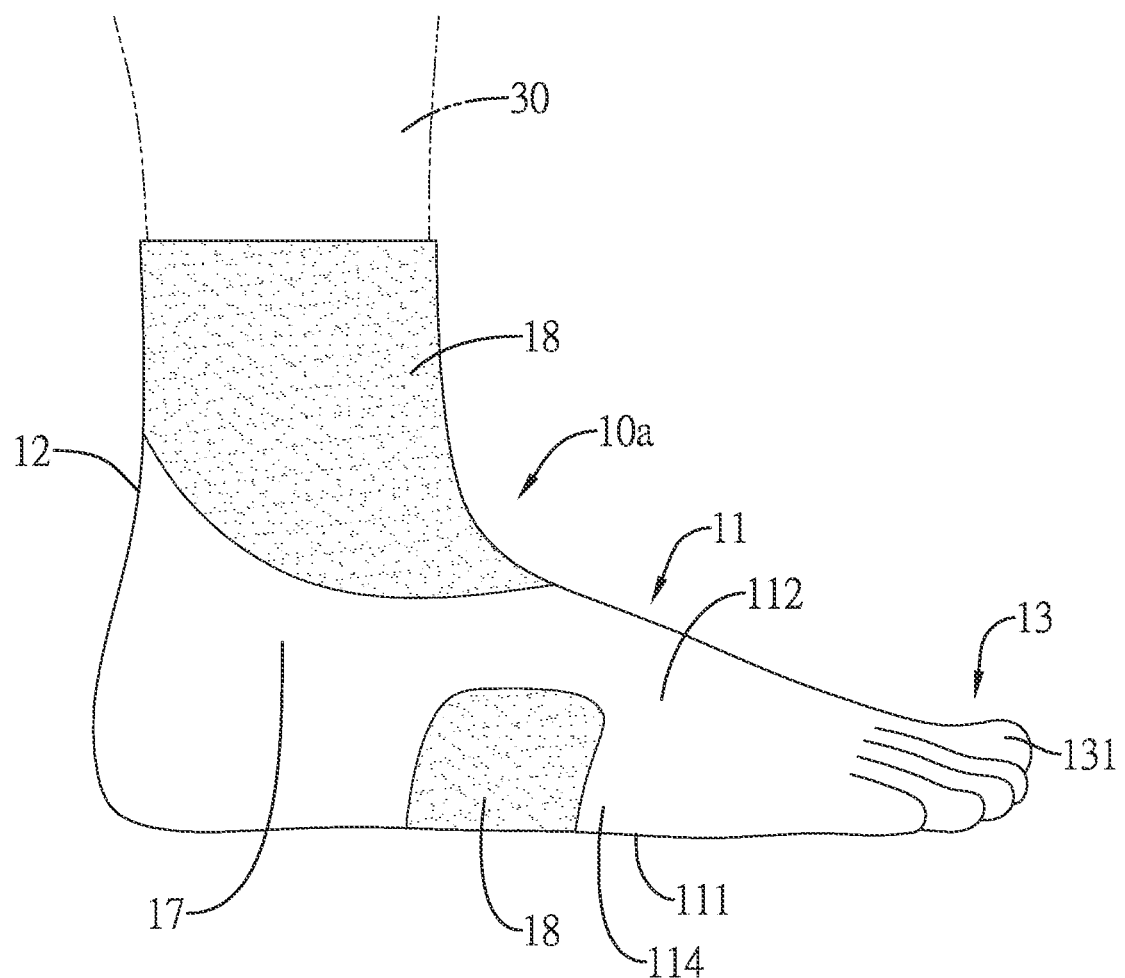
FIG. 3 is another side view of the flat foot orthosis in FIG. 1.
Figure 4:
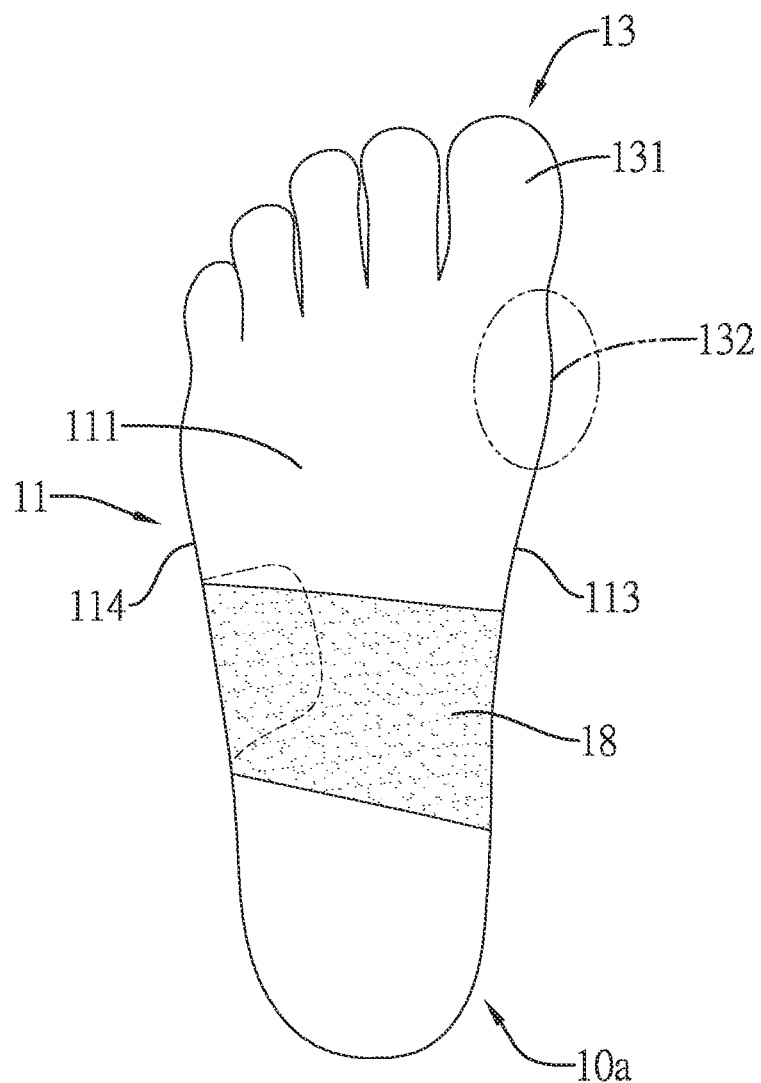
FIG. 4 is a bottom view of the flat foot orthosis in FIG. 1.
Figure 5:
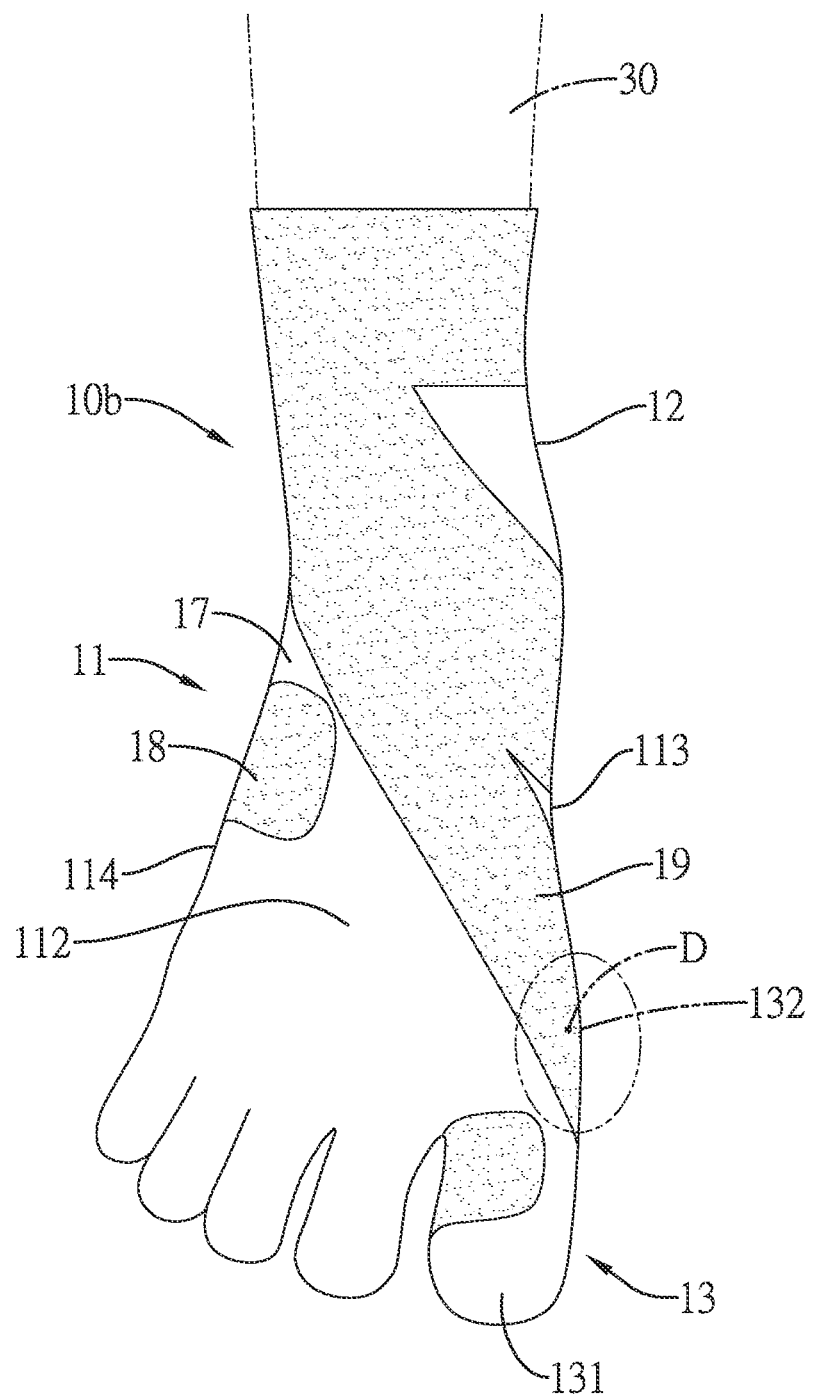
FIG. 5 is a front side view of a flat foot orthosis of a second embodiment in accordance with the present invention.
Figure 6:
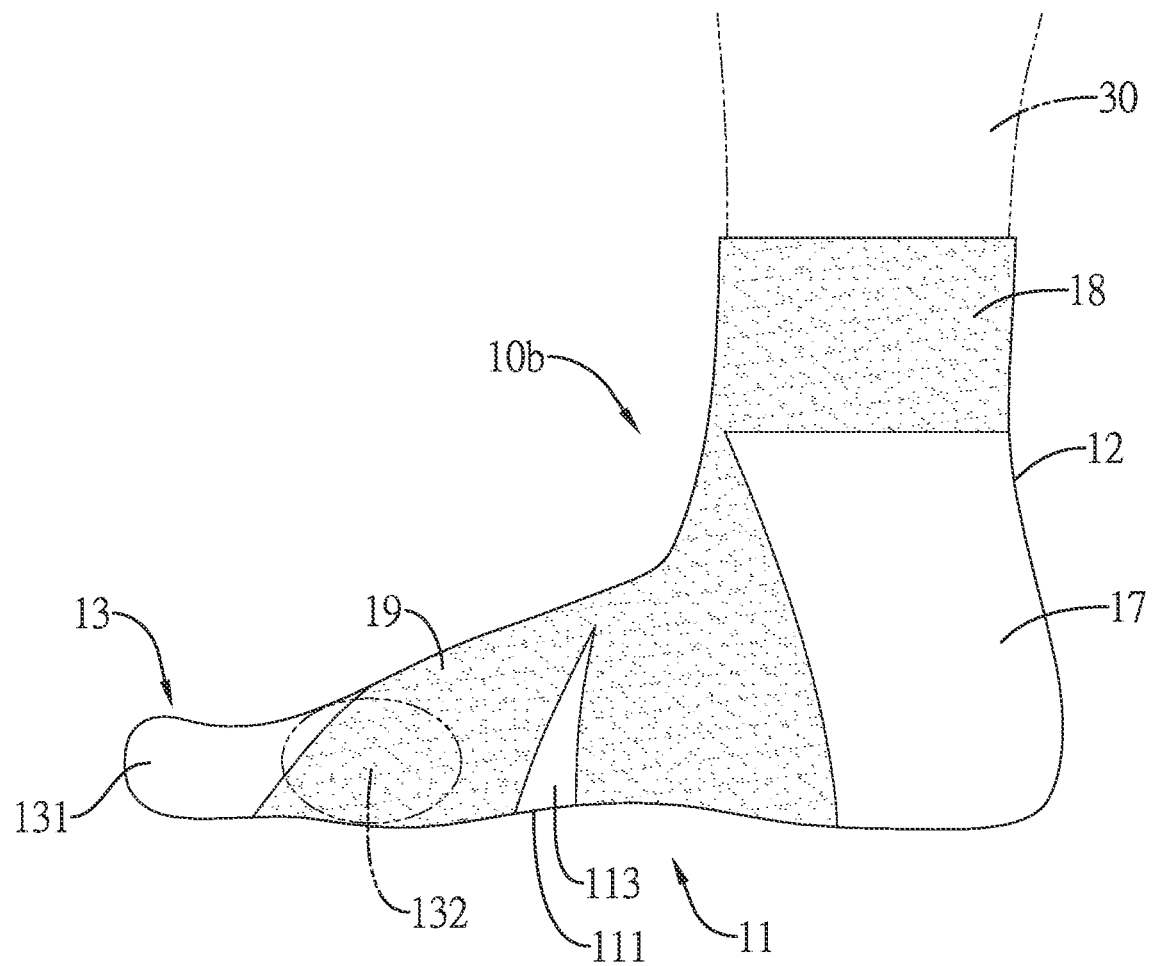
FIG. 6 is a side view of the flat foot orthosis in FIG. 5.
Figure 7:
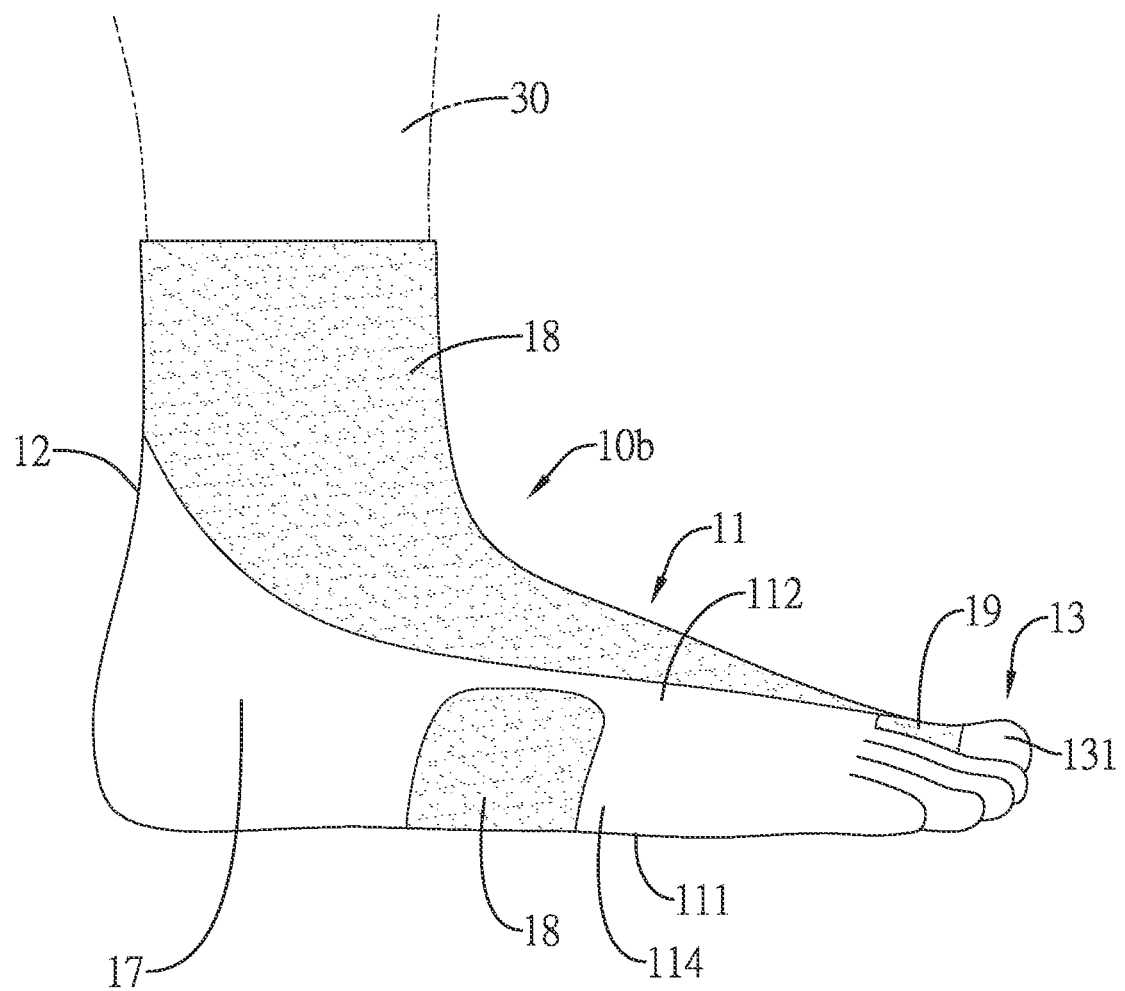
FIG. 7 is another side view of the flat foot orthosis in FIG. 5.
Figure 8:
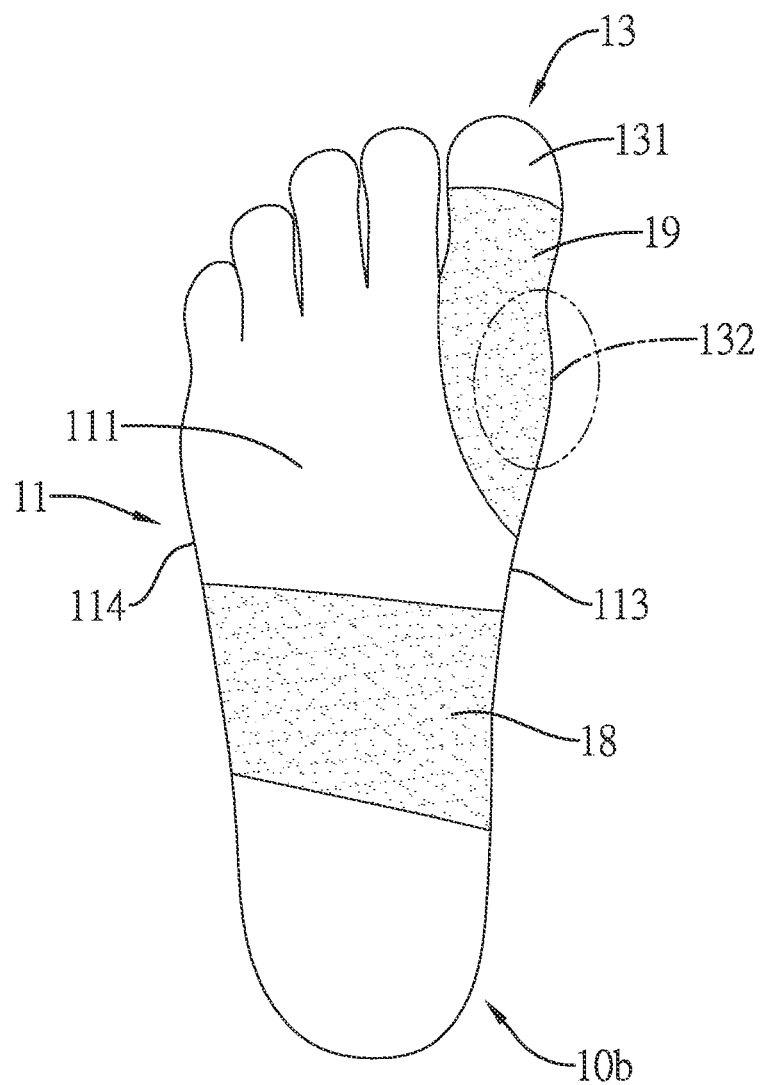
FIG. 8 is a bottom view of the flat foot orthosis in FIG. 5.
Figure 9:
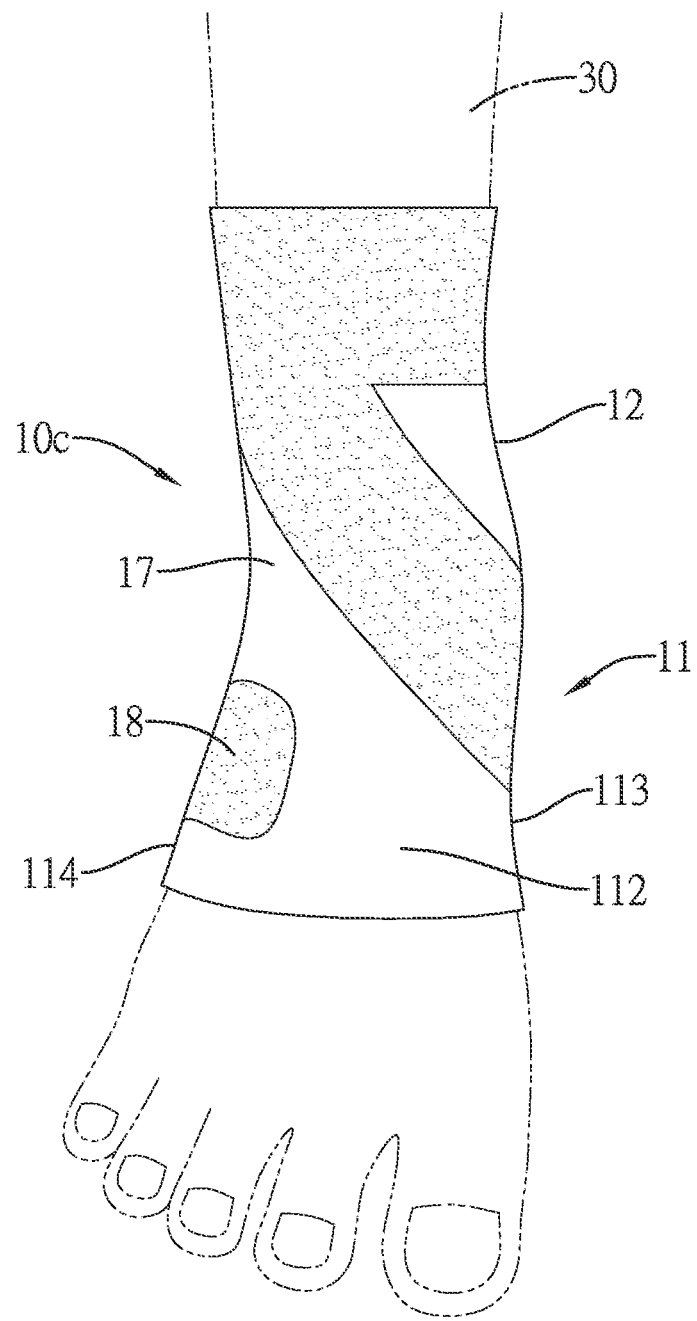
FIG. 9 is a front side view of a flat foot orthosis of a third embodiment in accordance with the present invention.
Figure 10:
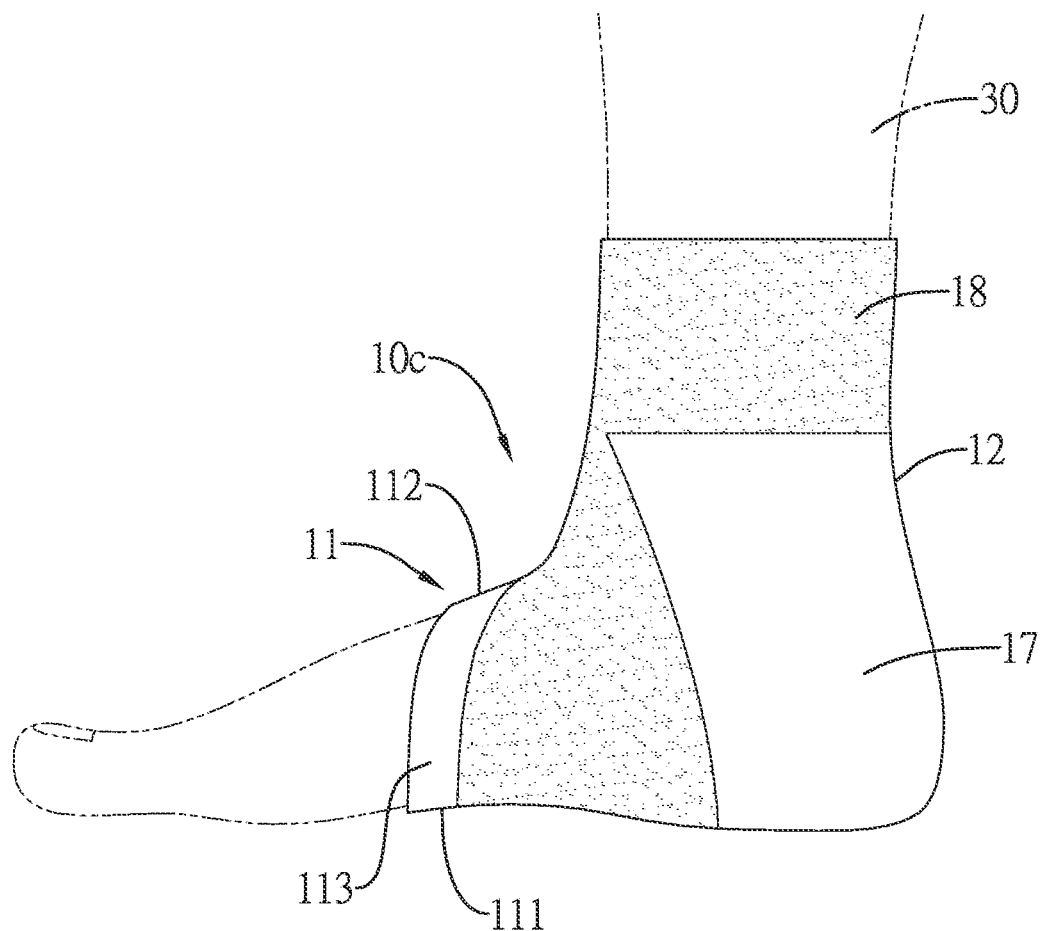
FIG. 10 is a side view of the flat foot orthosis in FIG. 9.

With reference to FIGS. 1, 5, 9, 11, 12, 14, and 15, the present invention provides five embodiments of a flat foot orthosis configured for correcting a flat foot. The flat foot orthosis in each one of the five embodiments comprises two bodies 10a, 10b, 10c, 10d, 10e. Each one of the two bodies 10a, 10b, 10c, 10d, 10e has a wearing space disposed inside, and comprises a foot portion 11, an ankle portion 12, and a shank portion 14. The foot portion 11 has a sole 111, an instep 112, an arch 113, and a lateral side 114. The sole 111 is located on a bottom of the foot portion 11. The instep 112 is located on a top of the foot portion 11. The sole 111 and the instep 112 vertically align with each other. The arch 113 and the lateral side 114 are located on two horizontal sides of the foot portion 11, wherein the arch 113 is on one of the two horizontal sides that faces the other one of the two bodies 10a, 10b, 10c, 10d, 10e. Each one of the arch 113 and the lateral side 114 is connected with the sole 111 and the instep 112. The ankle portion 12 is connected to the foot portion 11. The shank portion 14 is connected to the ankle portion 12.

Each one of the two bodies 10a, 10b, 10c, 10d, 10e has a substrate 17 and a first elastomer 18. The substrate 17 and the first elastomer 18 are disposed adjacent to each other, and wrap the wearing space of the body 10a, 10b, 10c, 10d, 10e. The substrate 17 extends from the foot portion 11 to the shank portion 14 through the ankle portion 12. The first elastomer 18 spirally extends along the substrate 17, and passes through the arch 113 of the foot portion 11.

With reference to FIGS. 1 to 4, 5 to 8, 9 and 10, 11 to 13, and 14 to 16, the first elastomer 18 is a single strip, has an end on the instep 112, extends spirally from the end, wraps over a cuboid bone A of a wearer 30, extends through the lateral side 114, the sole 111, and the arch 113 in order, and wraps over a navicular bone B of the wearer 30 at the arch 113. Afterwards the first elastomer 18 extends toward the shank portion 14, and wraps over a talus bone C of the wearer 30 at the ankle portion 12. The first elastomer 18 has a surrounding and fettering part located away from the end and configured for fettering the wearer. With reference to FIGS. 1 to 4, 5 to 8, 11 to 13, and 14 to 16, each one of the two bodies 10a, 10b, 10d, 10e of the first, the second, the fourth, and the fifth embodiments has a toe portion 13. The toe portion 13 is connected to a front end of the foot portion 11. The substrate 17 extends from the foot portion 11 to the toe portion 13. The toe portion 13 has five divisions for the wearer's five toes. Furthermore, with reference to FIGS. 1, 5, and 9, each one of the two bodies 10a, 10b, 10c of the first, the second, and the third embodiments has an opening located above the ankle portion 12, respectively a first opening, a second opening, and a third opening. The opening communicates with the wearing space. The surrounding and fettering part of the first elastomer 18 surrounds and fetters the shank portion 14 above the ankle portion 12.

With reference to FIGS. 5 to 8, the toe portion 13 comprises a hallux sheath 131. The hallux sheath 131 of the toe portion 13 is connected to the foot portion 11 at a hallux valgus region 132. The hallux valgus region 132 is located between the hallux sheath 131 and the arch 113 of the foot portion 11. Each one of the two bodies 10b has a second elastomer 19. The second elastomer 19 spirally extends toward the ankle portion 12 from the hallux sheath 131 at a top of the wearer's hallux, through a bottom of the wearer's hallux, further extends through and wraps the hallux valgus region 132, wraps over a $1^{st}$ metatarsal proximal phalangeal joint D of the wearer 30 at the hallux valgus region 132, and is connected to the first elastomer 18 at the instep 112.

Figure 11:
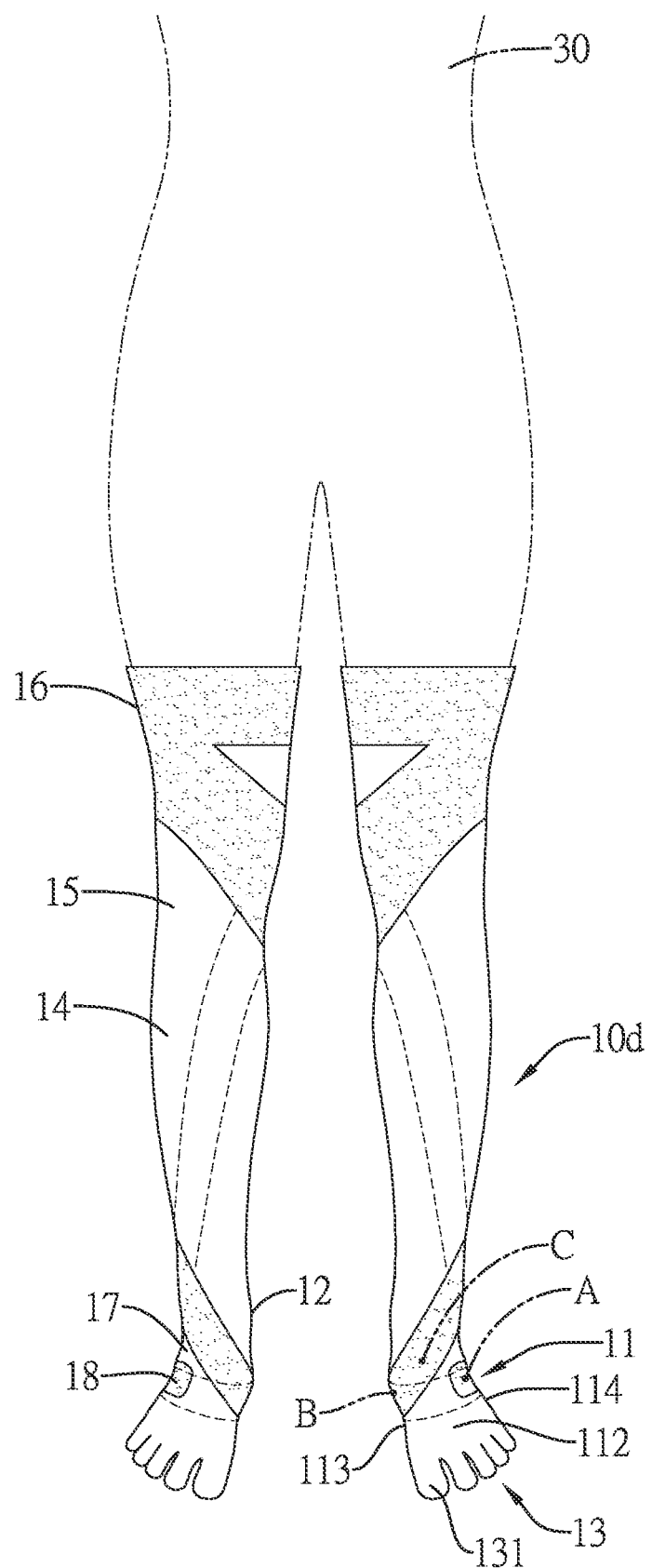
FIG. 11 is a front side view of a flat foot orthosis in a first configuration of a fourth embodiment in accordance with the present invention.
Figure 12:
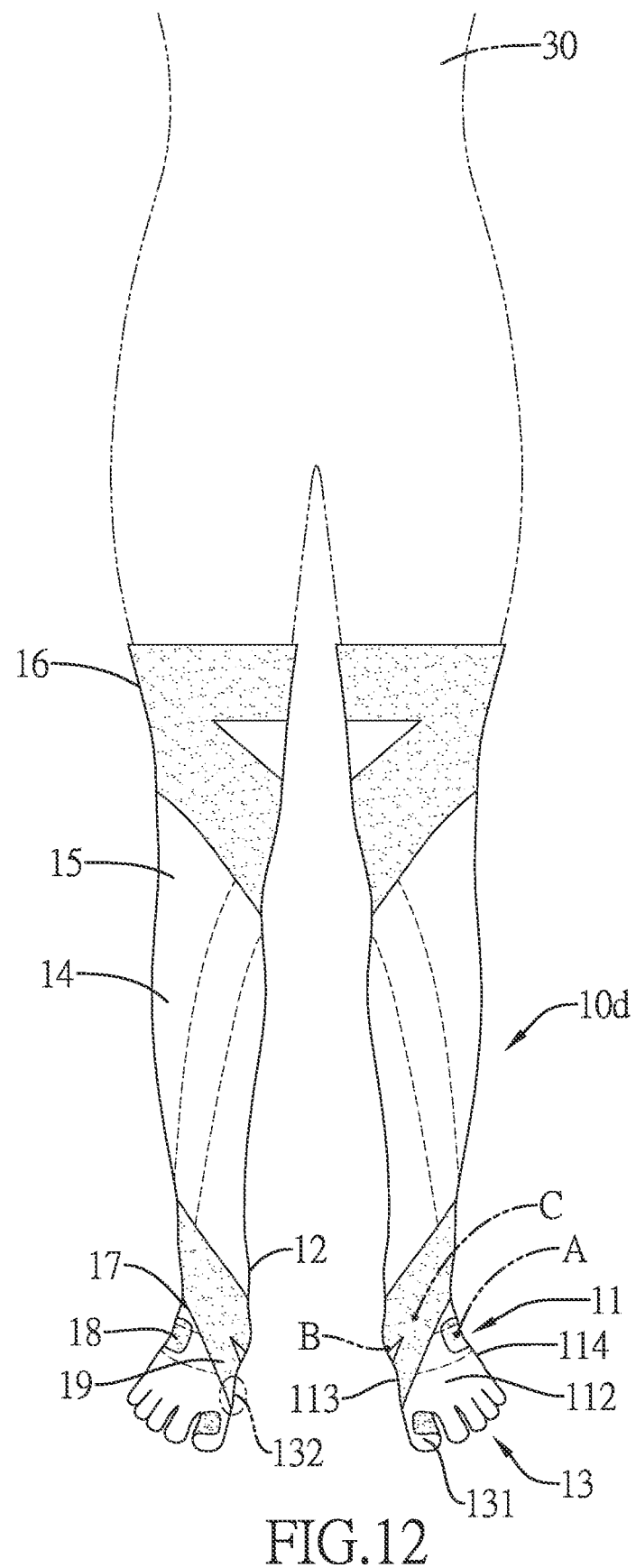
FIG. 12 is a front side view of a flat foot orthosis in a second configuration of the fourth embodiment in accordance with the present invention.
Figure 13:
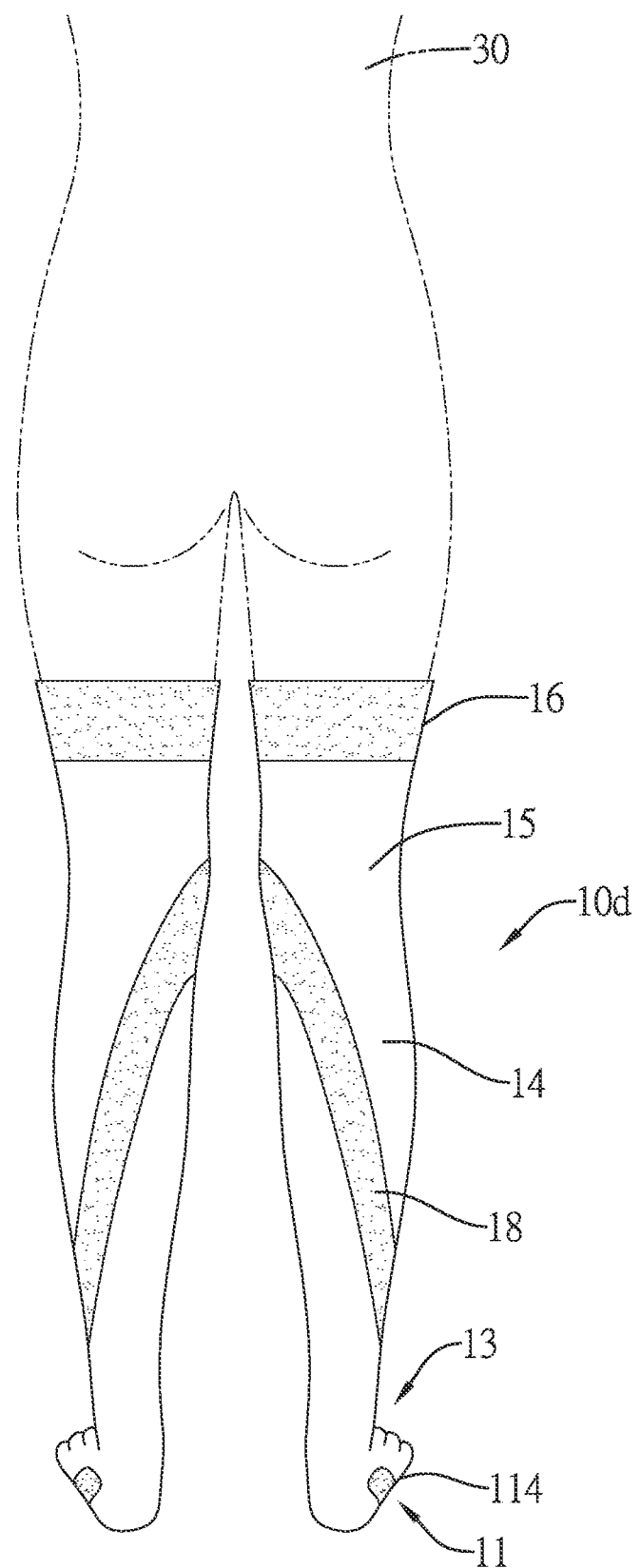
FIG. 13 is a rear side view of the flat foot orthosis in FIG. 11.

With reference to FIGS. 11 to 13, each one of the two bodies 10d has a knee portion 15 and a thigh portion 16. The knee portion 15 is connected to an upper end of the shank portion 14. The thigh portion 16 is connected to the knee portion 15, and is connected to the shank portion 14 through the knee portion 15. Based on the above-mentioned embodiments, the substrate 17 extends from the ankle portion 12 through the shank portion 14 and the knee portion 15, to the thigh portion 16. Each one of the two bodies 10d has a fourth opening located upon the thigh portion 16. The fourth opening communicates with the wearing space. With reference to FIGS. 12 and 13, the first elastomer 18, or the first elastomer 18 connected with the second elastomer 19, extends through a rear side of the shank portion 14, obliquely extends in combination with upward and inward turns through an inner side of the knee portion 15 in order, and the surrounding and fettering part of the first elastomer 18 of each one of the two bodies 10d surrounds and fetters the corresponding thigh portion 16.

Figure 14:
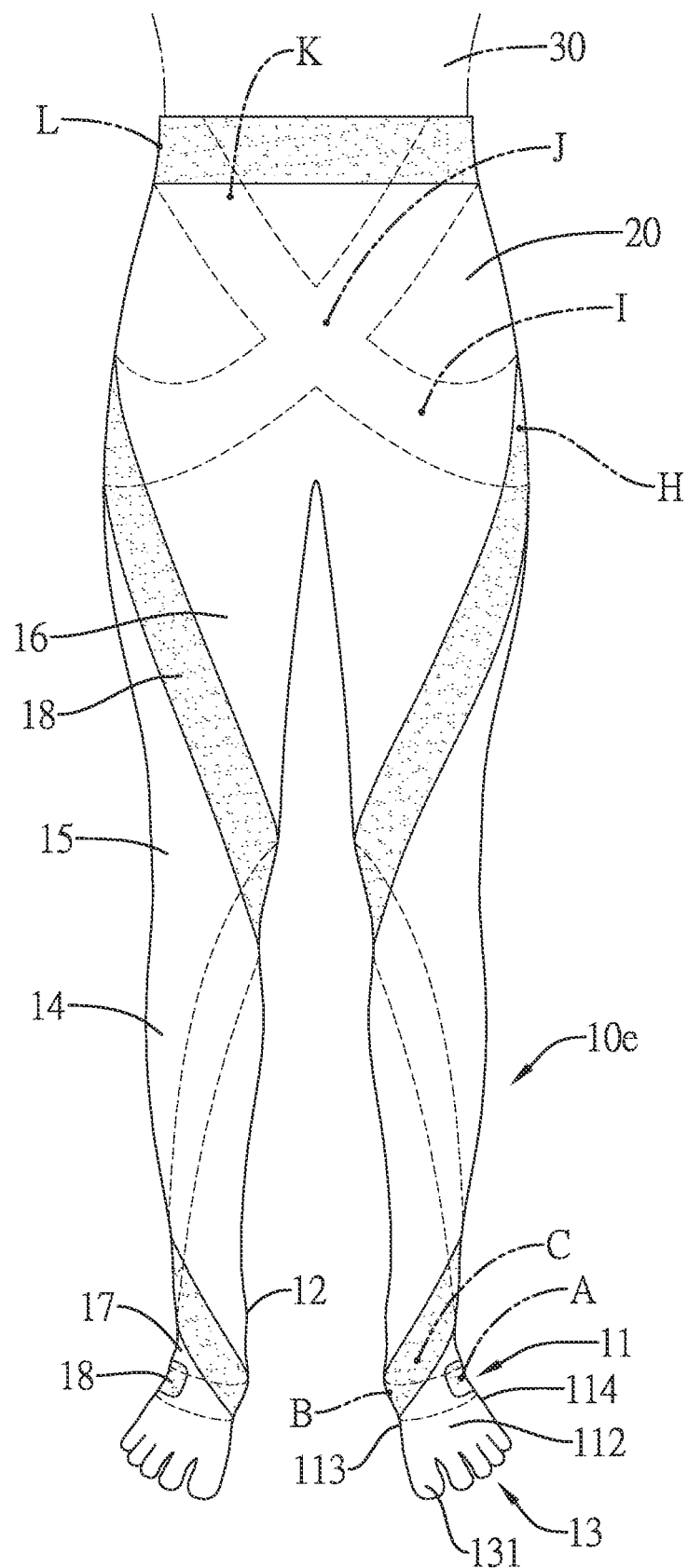
FIG. 14 is a front side view of a flat foot orthosis in a first configuration of a fifth embodiment in accordance with the present invention.
Figure 15:
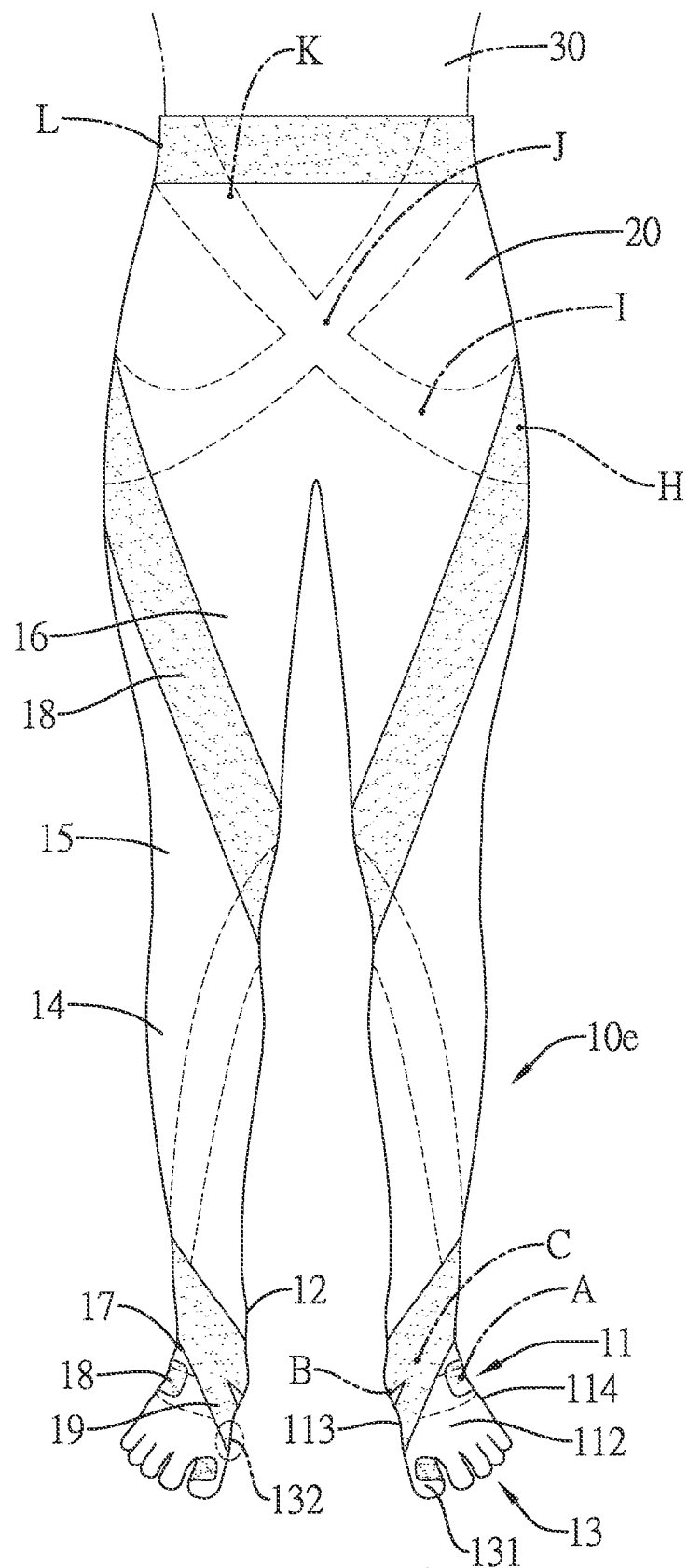
FIG. 15 is a front side view of a flat foot orthosis in a second configuration of the fifth embodiment in accordance with the present invention.
Figure 16:
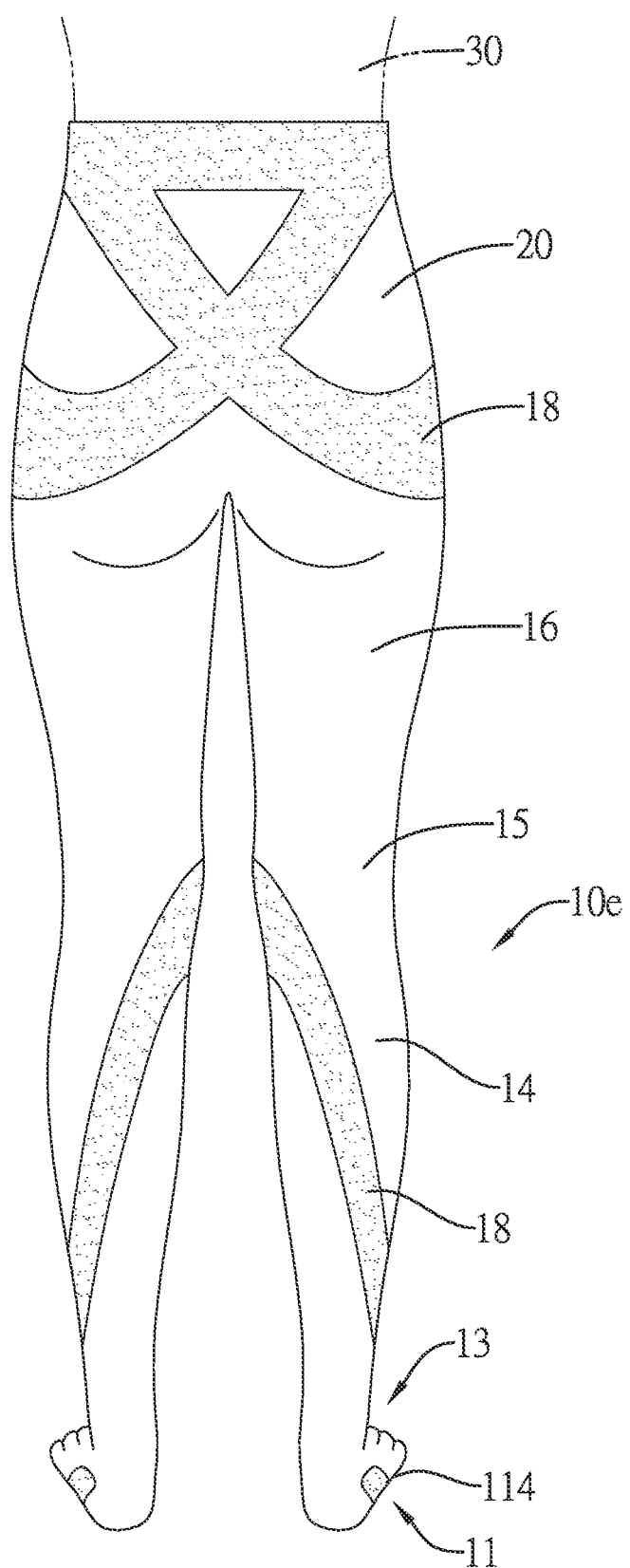
FIG. 16 is a rear side view of the flat foot orthosis in FIG. 14.
Figure 17:
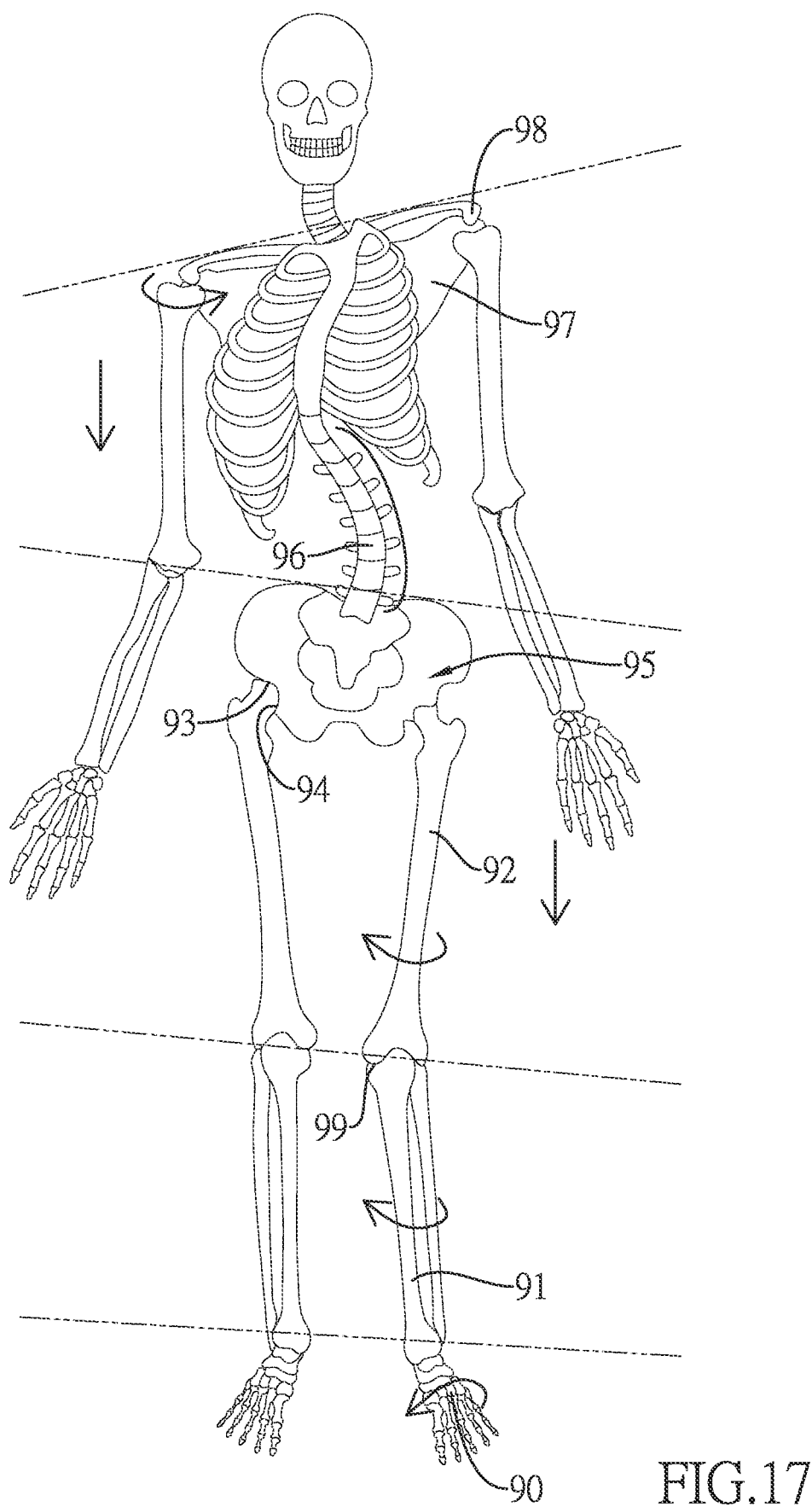
FIG. 17 shows disordered bone arrangements of a human body caused by an overpronated foot.
Figure 18A:
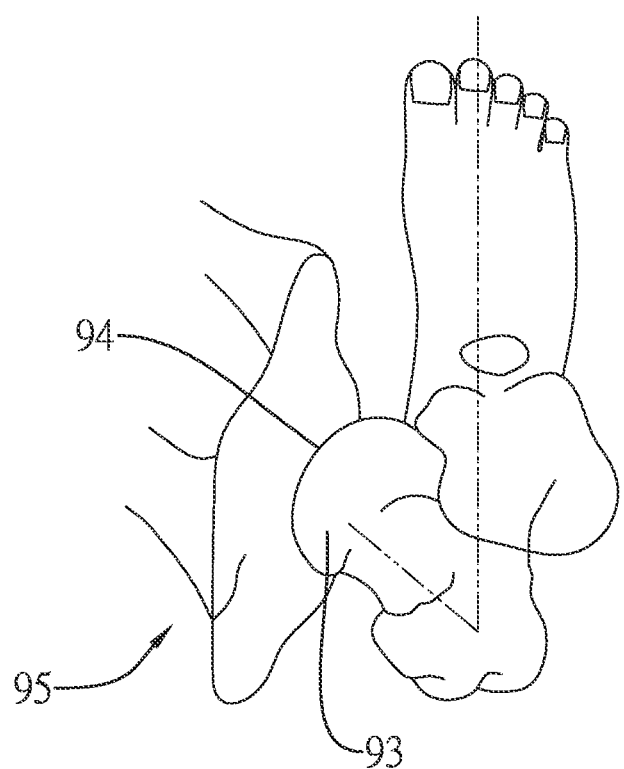
FIG. 18A shows a normal bone arrangement in a hip joint of a wearer.
Figure 18B:
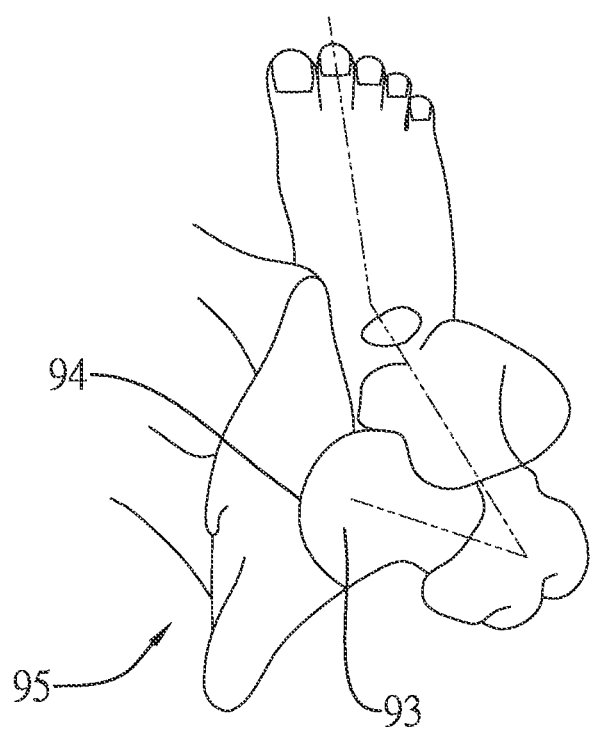
FIG. 18B shows a disordered bone arrangement in a hip joint of the wearer caused by the overpronated foot in FIG. 17.

With reference to FIGS. 14 to 16, each one of the two bodies 10e has a knee portion 15 and a thigh portion 16. The knee portion 15 is connected to an upper end of the shank portion 14. The thigh portion 16 is connected to the knee portion 15, and is connected to the shank portion 14 through the knee portion 15. Based on the aforementioned embodiments, the substrate 17 extends from the ankle portion 12, through the shank portion 14 and the knee portion 15, and to the thigh portion 16. The flat foot orthosis further comprises a pelvis portion 20. The pelvis portion 20 is connected with upper ends of the two thigh portions 16 of the two bodies 10e. The pelvis portion 20 has a fifth opening communicating with the wearing spaces of the two bodies 10e.

With reference to FIGS. 15 and 16, the first elastomer 18, or the first elastomer 18 connected with the second elastomer 19, extends through a rear side of the shank portion 14, obliquely extends in combination with upward and inward turns through an inner side of the knee portion 15, and extends through a front side of the thigh portion 16 in order, spirally extends through the pelvis portion 20, wraps a hip joint H of the wearer 30, and wraps over an Ischia I, a sacrum J, a sacroiliac joint K, and an iliac crest L of the wearer 30 at a rear side of the pelvis portion 20. The two first elastomers 18 intersect with each other at the rear side of the pelvis portion 20, and the two surrounding and fettering parts of the two first elastomers 18 surround and fetter where the wearer's pelvis and the wearer's waist meet.

The flat foot orthosis may provide the wearer 30 with an effect of bone and joint alignment correction. With reference to FIGS. 1 to 4, 5 to 8, 9 and 10, 11 to 13, and 14 to 16, after the wearer 30 puts on the two bodies 10a, 10b, 10c, 10d, 10e, the foot portions 11 cover the wearer's feet, wherein the arches 113 cover the wearer's medial arches, the insteps 112 cover the wearer's insteps, and the soles 111 cover and are located under the wearer's soles. The ankle portions 12 and the shank portions 14 are sheathed on the wearer's ankles and shanks, respectively. The first elastomer 18 of each one of the two bodies 10a, 10b, 10c, 10d, 10e extends outwardly and downwardly from the instep 112 through the lateral side 114. Then the first elastomer 18 extends toward the ankle portion 12 through the sole 111 and the arch 113 in order. Therefore, the first elastomer 18 may provide a stretching and pressing force on the wearer's medial arch, and the overpronated foot of the wearer 30 may be corrected to normal.

With reference to FIGS. 5 to 8, 12, and 15, the second elastomer 19 of each one of the second, the fourth, and the fifth embodiments extends from a bottom of the hallux sheath 131 to a top of the hallux sheath 131, extends through the hallux valgus region 132, and further extends toward the ankle portion 12 through the instep 112. Thereby the second elastomer 19 may provide a stretching and pressing force to correct hallux valgus that may occur at the hallux valgus region 132.

With reference to FIGS. 11 to 13, in the fourth embodiment, the first elastomer 18 further extends through the knee portion 15 and the thigh portion 16. Consequently, the first elastomer 18 may provide a torque to the wearer's shank and the wearer's thigh to externally rotate, and provide an outward pushing force to correct knee valgus.

With reference to FIGS. 14 to 16, in the fifth embodiment, the first elastomer 18 extends from the shank portion 14 through the inner side of the knee portion 15, and further extends through the thigh portion 16 to the pelvis portion 20. In addition to the described benefits of the fourth embodiment, the first elastomer 18 may provide an externally rotating torque and a pressing force for the hip joint H to correct pelvic tilt and torsion due to internal rotated femur and backwardly pushed acetabulum of the pelvis of the wearer 30.

With reference to FIGS. 1 to 4, 5 to 8, 9, and 10, the two bodies 10a, 10b, 10c of the flat foot orthosis may be configured as socks or ankle braces. The first elastomer 18 thereof fetters the shank portion 14 that is above the ankle portion 12, so the first elastomer 18 may be thereby stretched and fixed to provide a stretching and pressing force. Moreover, with reference to FIGS. 11 to 13, and 14 to 16, the flat foot orthosis is configured as over-the-knee socks or pantyhose.

With the aforementioned technical characteristics, the flat foot orthosis utilizes the first elastomers 18 to stretch the arch 113, further to push the knee portion 15, or to rotate the pelvis portion 20 to apply corrective forces on relevant parts of the wearer 30. Therefore, appropriate bone and joint alignments and proper biomechanics may be continued to maintain for the wearer 30. Poor postures, and subsequent discomfort and muscular sores & pains due to disordered bone and joint alignments may be alleviated. Consequently, after the flat foot has been corrected by the present invention, the wearer 30 improves health and better postures.

When the wearer 30 wears the flat foot orthosis, the first elastomers 18 may provide the stretching and pressing forces to pull the wearer's medial arches, to maintain correct bone and joint alignments of the lower limbs, the knee joint, the hip joint H, the pelvis, and to prevent hallux valgus, functional flat feet, and pelvic tilt and torsion.

Even though several characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. A flat foot orthosis configured for correcting a flat foot, and the flat foot orthosis comprising:
  two bodies, each one of the two bodies having
    a wearing space disposed inside the respective body;
    a foot portion having
      a sole located on a bottom of the foot portion;
      an instep located on a top of the foot portion;
      an arch located on a first of two horizontal sides of the foot portion, facing the other one of the two bodies, and connected to the sole and the instep; and
      a lateral side located on a second of the two horizontal sides of the foot portion, and connected to the sole and the instep;
    an ankle portion connected to the foot portion;
    a shank portion connected to the ankle portion;
    a knee portion connected to the shank portion;

a thigh portion connected to the knee portion;
a toe portion connected to a front end of the foot portion, and having a hallux sheath;
a hallux valgus region located between the hallux sheath and the arch of the foot portion;
a substrate surrounding the wearing space, and extending from the toe portion to the thigh portion through the foot portion, the ankle portion, the shank portion, and the knee portion;
a first elastomer being a single strip, disposed adjacent to the substrate, surrounding the wearing space, having an end located on the instep of the foot portion and configured for placement at a cuboid bone of a wearer, extending spirally from the end through the lateral side, the sole, and the arch in order, configured for wrapping over a navicular bone of the wearer and extending through the ankle portion and configured for placement at a talus bone of the wearer, extending through a rear side of the shank portion, obliquely extending in combination with upward and inward turns through an inner side of the knee portion, and spirally extending through the thigh portion; and
a second elastomer configured for extending from the hallux sheath at a top of the wearer's hallux, through a bottom of the wearer's hallux, further extending upwardly through and wrapping the hallux valgus region, through the instep toward the ankle portion, and connecting to the first elastomer;
a pelvis portion connected to the thigh portion of each of the two bodies, having an opening communicating with the wearing space of each of the two bodies and configured for wrapping over a hip joint of the wearer;
wherein the first elastomer of each one of the two bodies spirally extends from the thigh portion to the pelvis portion, is configured for wrapping the hip joint of the wearer, intersecting with the first elastomer of the other one of the two bodies at a rear side of the hip of the wearer behind the pelvis of the wearer, extending and wrapping over a sacroiliac joint and an iliac crest of the wearer, and has a surrounding and fettering part located away from the end, so that the first elastomer is configured to provide a stretching and pressing force on the medial arch of the wearer, pulling the medial arch of the wearer;
the surrounding and fettering part of the first elastomer of each of the two bodies being configured to surround and fetter where the pelvis and the waist of the wearer meet.

* * * * *